(12) United States Patent
Molema et al.

(10) Patent No.: US 8,118,194 B2
(45) Date of Patent: Feb. 21, 2012

(54) CARTRIDGE FOR AN APPLIANCE FOR PERSONAL CARE AND AN APPLIANCE COMPRISING SUCH A CARTRIDGE

(75) Inventors: Jeroen Molema, Drachten (NL); Wilko Westerhof, Drachten (NL); Anke Sinnema, Drachten (NL); Johannes Josephus Blaak, The Hague (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 963 days.

(21) Appl. No.: 11/917,895

(22) PCT Filed: Jun. 6, 2006

(86) PCT No.: PCT/IB2006/051799
§ 371 (c)(1),
(2), (4) Date: Dec. 17, 2007

(87) PCT Pub. No.: WO2006/134514
PCT Pub. Date: Dec. 21, 2006

(65) Prior Publication Data
US 2008/0216322 A1    Sep. 11, 2008

(30) Foreign Application Priority Data
Jun. 16, 2005    (EP) .................................... 05105295

(51) Int. Cl.
*B65D 37/00* (2006.01)
*B67D 7/06* (2010.01)
*B67B 1/00* (2006.01)
*B26B 19/44* (2006.01)
*B05B 11/02* (2006.01)

(52) U.S. Cl. .......... 222/207; 222/183; 222/214; 30/41.5

(58) Field of Classification Search ............... 222/207, 222/205, 214, 213, 206, 209, 400.5, 190, 222/191, 630, 632, 192, 183, 153.01, 153.03, 222/153.13, 386.5, 211, 212, 215; 30/41, 30/41.5, 541
See application file for complete search history.

(56) References Cited

U.S. PATENT DOCUMENTS

| | | | | |
|---|---|---|---|---|
| 3,716,091 A | * | 2/1973 | Gaines | 206/37.8 |
| 3,822,906 A | * | 7/1974 | Gaines | 292/251.5 |
| 4,641,945 A | * | 2/1987 | Ikesue et al. | 399/262 |
| 5,398,850 A | * | 3/1995 | Sancoff et al. | 222/386.5 |
| 5,553,741 A | * | 9/1996 | Sancoff et al. | 222/1 |
| 5,558,255 A | * | 9/1996 | Sancoff et al. | 222/189.06 |
| 5,571,261 A | * | 11/1996 | Sancoff et al. | 222/386.5 |

(Continued)

FOREIGN PATENT DOCUMENTS
EP    1157792    11/2001
(Continued)

*Primary Examiner* — Kevin P Shaver
*Assistant Examiner* — Stephanie E Williams

(57) ABSTRACT

A cartridge for an appliance for personal care, such as skin, dental or hair treatment includes a main body, a dispensing structure for dispensing a substance, such as a liquid, a paste or a gel, and a cartridge detachably connected to the main body. The cartridge bounds a reservoir space for holding the substance to be dispensed and includes a flexible wall part bounding the reservoir space for allowing reservoir space volume to accommodate to a volume of the substance filled therein and volumes of the substance dispensed therefrom; a rigid wall part also bounding the reservoir space, and a rigid housing. The flexible wall part is connected to the rigid housing along a contour of the rigid wall part.

17 Claims, 4 Drawing Sheets

U.S. PATENT DOCUMENTS

Figure 1:
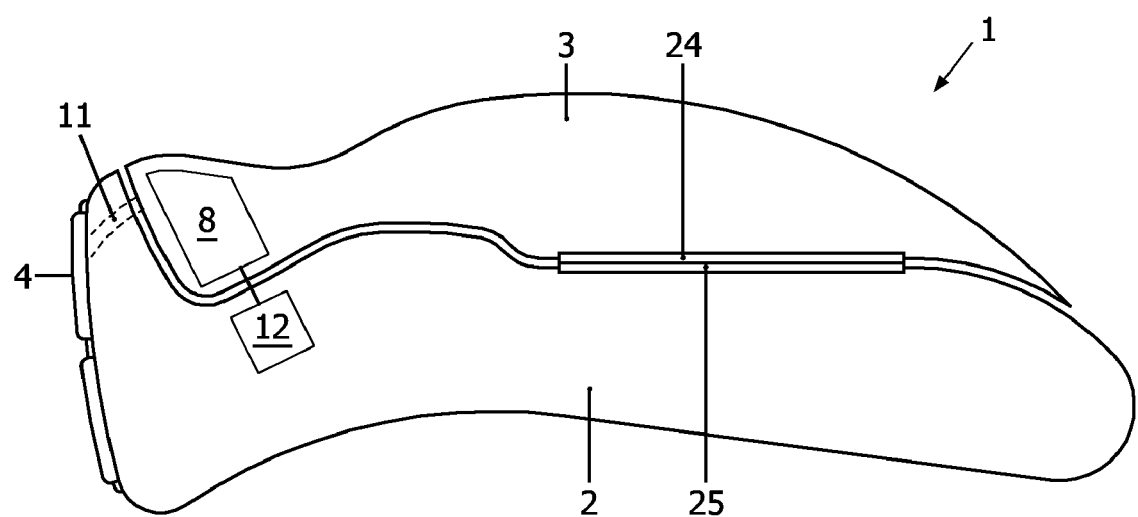

| | | | |
|---|---|---|---|
| 5,588,556 A * | 12/1996 | Sancoff et al. | 222/1 |
| 5,700,245 A * | 12/1997 | Sancoff et al. | 604/145 |
| 5,814,020 A * | 9/1998 | Gross | 604/141 |
| 6,131,288 A * | 10/2000 | Westerhof et al. | 30/41 |
| 6,308,413 B1 | 10/2001 | Westerhof et al. | |
| 6,312,436 B1 * | 11/2001 | Rijken et al. | 606/133 |
| 6,354,005 B1 * | 3/2002 | Bosch | 30/43.6 |
| 6,612,819 B1 | 9/2003 | Furst et al. | |
| 6,792,695 B2 * | 9/2004 | Fry et al. | 34/597 |
| 6,913,606 B2 * | 7/2005 | Saitou et al. | 606/133 |
| 6,983,866 B2 * | 1/2006 | Smart et al. | 222/192 |
| 7,163,013 B2 * | 1/2007 | Harrison | 128/203.21 |
| 7,402,165 B2 * | 7/2008 | Saitou et al. | 606/133 |
| 7,438,202 B2 * | 10/2008 | Gross | 222/214 |
| 7,753,884 B2 * | 7/2010 | Gallnbock | 604/147 |
| 2002/0032964 A1 * | 3/2002 | Westerhof et al. | 30/41 |

FOREIGN PATENT DOCUMENTS

| | | |
|---|---|---|
| EP | 1157792 A1 | 11/2001 |
| EP | 1252980 | 10/2002 |
| EP | 1252980 A2 | 10/2002 |
| WO | 9855274 | 12/1998 |
| WO | 03068466 | 8/2003 |
| WO | 03068466 A1 | 8/2003 |
| WO | 2004050313 | 6/2004 |
| WO | 2004050313 A1 | 6/2004 |

* cited by examiner

CARTRIDGE FOR AN APPLIANCE FOR PERSONAL CARE AND AN APPLIANCE COMPRISING SUCH A CARTRIDGE

The invention relates to a cartridge for an appliance for personal care, such as skin, dental or hair treatment, comprising a dispensing structure for dispensing a substance, such as a liquid, paste or gel. The invention also relates to an appliance including such a cartridge.

An example of such a cartridge and such an appliance is disclosed in European patent application 1 252 980. In this document, the appliance is a shaver. This known shaver includes a lotion-feeding module that is detachable from a housing of the shaver. The module includes a shell, a flexible tank containing a lotion to be dispensed, and a pressurizer in the form of a plate, which is pressed against the tank by a leaf spring formed on back of the pressurizer in close contact with the housing. When the module is detached from the housing, the pressurizer can be detached from the shell in order to take out the tank for refilling the lotion or replacement of the tank itself.

Removal of an empty tank and replacing it by a filled tank requires several user actions, some of which require particular care. Taking out an empty tank requires detaching the module and removing the tank from other parts of the module. The installation of the flexible, filled tank requires proper insertion and assembly of the tank to the other parts of the module. After installing a filled tank in the module, the module needs to be re-attached to the housing of the shaver.

It is an object of the invention to facilitate replacement of an empty reservoir of a personal care appliance, while offering a compact, low-cost solution.

The connection of the flexible wall part to the rigid housing along the contour of the rigid wall part causes the reservoir to have a generally fixed shape that deforms relatively little during handling while the reservoir is nevertheless flexible enough to accommodate volume variations as the reservoir is filled with the substance and as the substance is dispensed from the reservoir. Moreover, the rigid housing at least contributes to the rigidity of the rigid wall part, which may be part of the rigid housing or attached thereto so as to be of a shape that is generally fixed during use. The reservoir can easily be replaced by replacing the cartridge as a whole.

Figure 2:
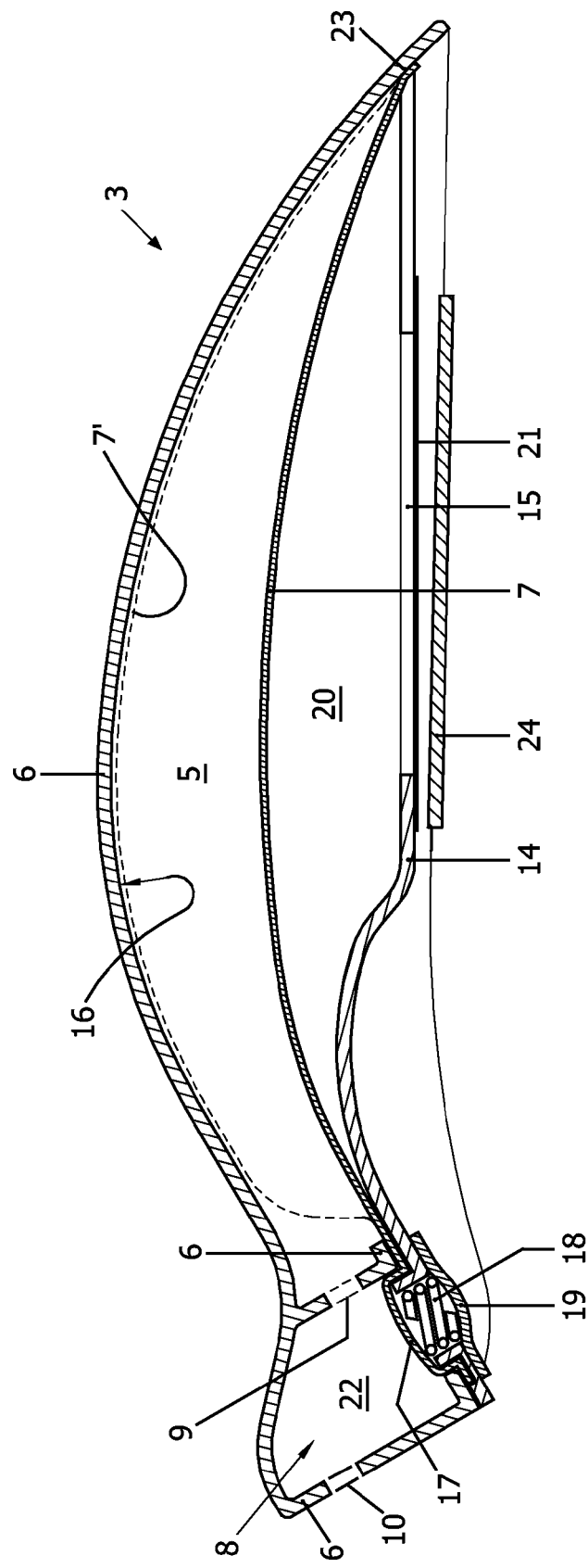
Figure 3:
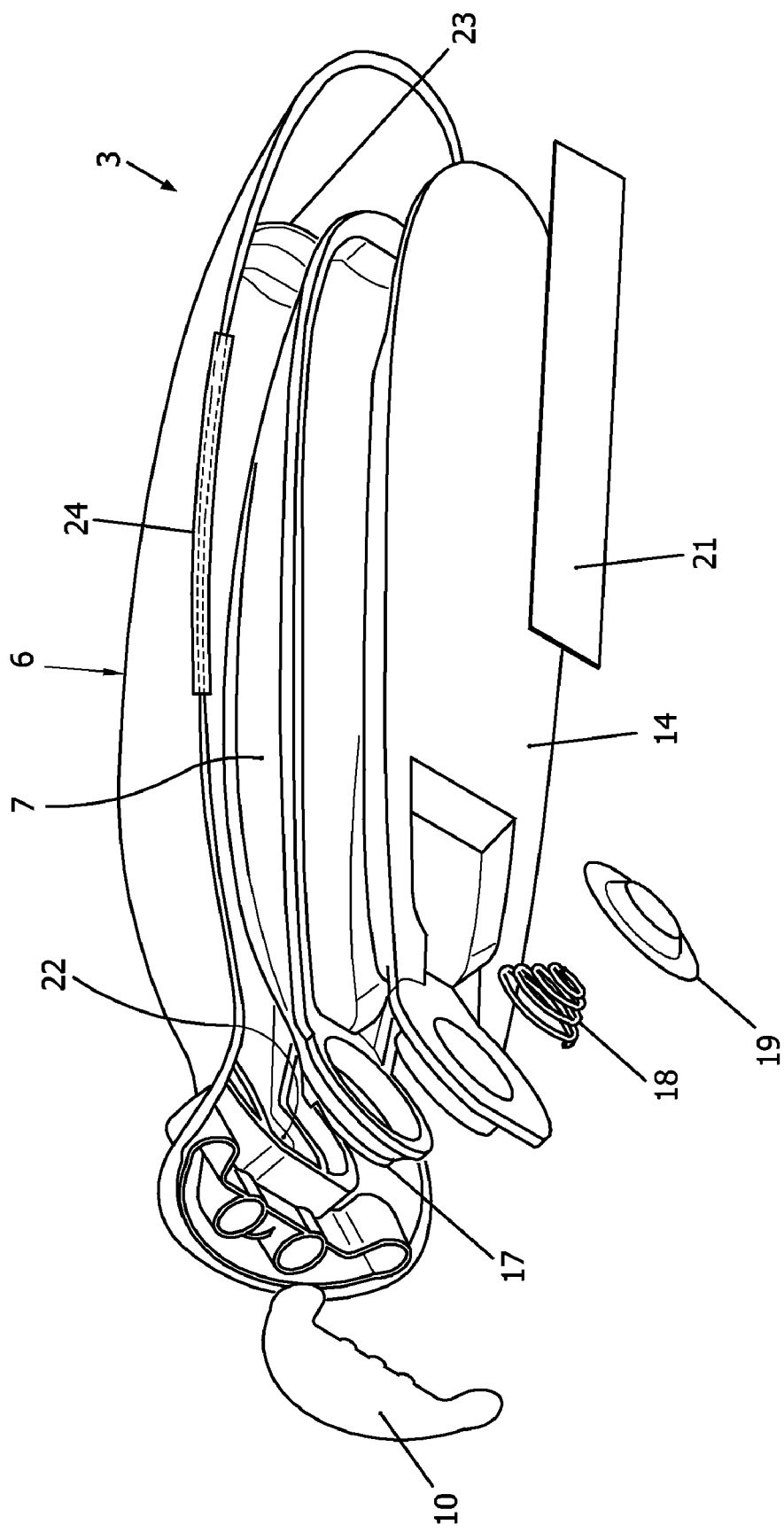
Figure 4:
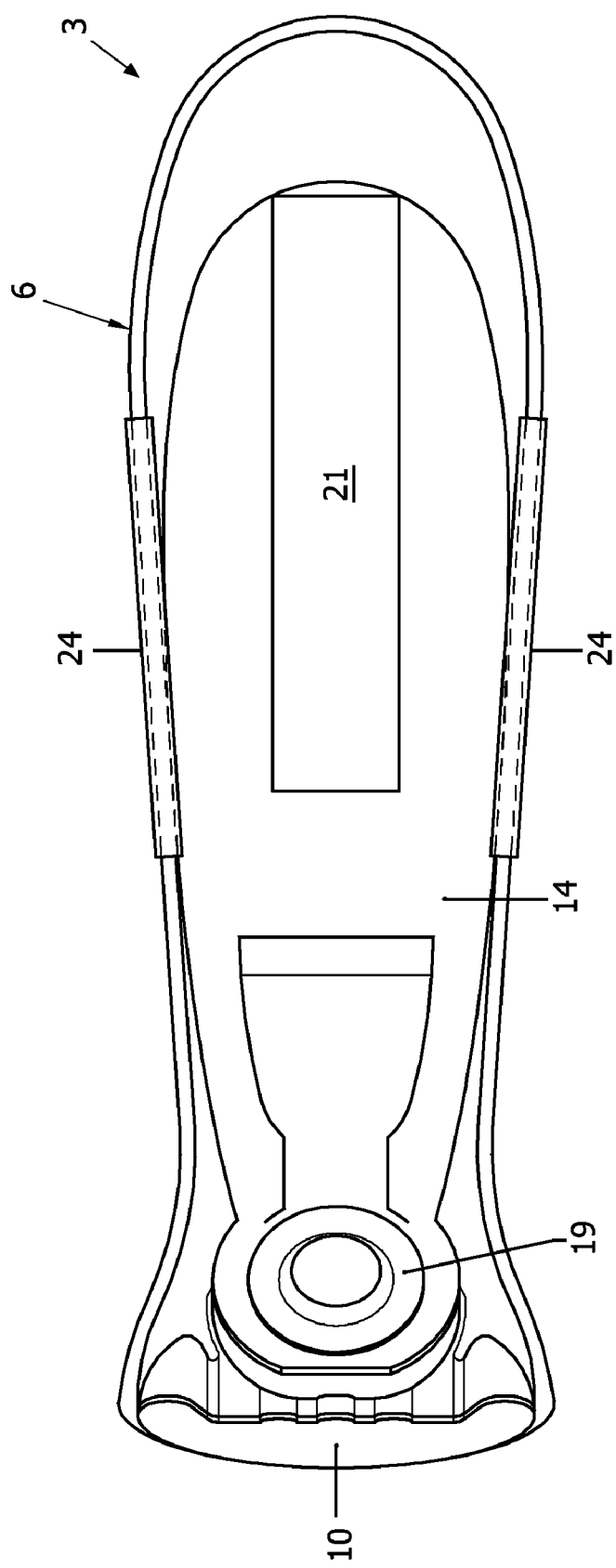

Further features, effects and details of embodiments of the invention are described below with reference to the accompanying schematical drawings, in which:

FIG. 1 is a schematic side view of an example of an appliance according to the invention, FIG. 2 is a cross-sectional view of a cartridge for the appliance shown in FIG. 1, FIG. 3 is an exploded view of the cartridge shown in FIG. 2, and FIG. 4 is a bottom view of the cartridge shown in FIGS. 2 and 3.

In the present description, the invention is described with reference to an example in the form of a shaver and a cartridge for use as part of such a shaver. However, within the framework of the present invention, the appliance may also be in the form of a different type of appliance for personal care in which a substance, such as a liquid, a paste, a gel or the like is dispensed, for example an epilator, a toothbrush or a hair styler. For the purpose of shaving, the substance may for instance be a lubricant in liquid, paste or gel form that reduces the friction between, on the one hand, a shaving head and cutters and, on the other hand, the skin. The lubricant may also have cosmetic and/or therapeutic effects on the skin, such as moisturizing and disinfecting.

The shaver 1 according to the example shown in FIG. 1 has a main body 2 and a cartridge 3. The main body 2 carries three shaving heads 4 in which movable cutters can be driven by a motor inside the main body 2. The shaver comprises a dispensing structure for dispensing a substance, such as a shaving gel or lotion. The cartridge 3, shown in more detail in FIGS. 2-4, is comprised in this dispensing structure, but it is in principle also possible that the dispensing structure is partially arranged in the main body.

The cartridge 3 has a rigid housing, which, in the shown example, is formed by an outer housing part 6 and an inner housing part 14. A reservoir space 5 for the substance to be dispensed is located in the cartridge 3.

In the example, the dispensing structure further includes a pump 8. The pump 8 has a one-way inlet valve 9 via which the pump chamber 22 communicates with the reservoir space 5 and a one-way outlet valve 10 via which the pump chamber 22 communicates with a passageway 11 extending through the main body 2 and having an outlet opening in the area of the shaving heads 4 when the cartridge 3 is coupled to the main body 2 of the shaver. The pump 8 is equipped with a pump membrane 17 in contact with a spring 18 to implement the pumping effect. In turn, the spring is in contact with a pump plate 19.

In use, the pump 8 is actuated by a drive mechanism 12 in the main body 2, which is coupled to the motor. The drive mechanism 12 imparts reciprocating movement upon the pump plate 19. The spring 18 transfers at least part of the motion imparted upon the pump plate 19 to the pump membrane 17, causing at least a portion of the pump membrane 17 to move to and fro, thereby alternatingly enlarging and reducing the internal volume of the pump chamber 22. The spring 18 avoids the need of close tolerances between the location and stroke of the drive mechanism 12 and the location and stroke of the pump membrane 17.

When operated, the pump 8 draws substance from the reservoir space 5 and presses the substance into the passageway 11. Via the passageway 11, the substance pumped out of the reservoir 5 is led to the user's skin when the shaver is in use. Because the pump 8 is integrated in the cartridge 3, a separate seal between the pump 8 and the cartridge 3 is not necessary and mounting of the cartridge is facilitated, because it does not need to be connected to a pump.

The reservoir space 5 for holding the substance to be dispensed is bounded by a flexible wall part 7 and a rigid wall part 16. The rigid wall part 16 generally keeps the reservoir space 5 in its basic shape while the flexible wall part 7 is flexible to such an extent that it allows the reservoir space volume to accommodate to volumes of the substance filled therein and dispensed therefrom. In FIG. 2, the flexible wall part 7 is shown in an intermediate position between its position when the reservoir is completely full and its position when the reservoir is completely empty. The term "rigid" is not to be interpreted as absolutely or extremely non-deformable, but merely as more rigid than the flexible wall part 7, so that accommodation to changes in the amount of substance in the reservoir space 5 occurs predominantly by deformation of the flexible wall part 7, while the rigid wall part 16 is at least rigid enough to generally keep the reservoir space from being folded or the like, for instance during manual manipulation when an empty cartridge 3 is replaced by a new, full cartridge 3. The rigidity of the rigid wall part 16 may for instance be comparable to the rigidity that is common for housing parts of domestic appliances such as shavers and the like.

The flexible wall part 7 connects to the rigid housing 6, 14 along a contour 23 of the rigid wall part 16. This prevents substantial deformation of the flexible wall part during handling, so that handling of the reservoir requires no fumbling with a flexible bag and the reservoir can easily be connected. Nevertheless, the reservoir is flexible enough to accommodate to volume variations as the reservoir is filled and as substance is dispensed from the reservoir. Moreover the rigid housing 6, 14 at least contributes to the rigidity of the rigid wall part 16 which, according to the present example, is part of the rigid housing 6, 14. It is however also possible to provide that the rigidity of the rigid wall part is at least mainly provided by suitable attachment of that wall part to the rigid housing, for instance over its entire surface or in suitably distributed areas.

Because a portion of the rigid housing 6, 14 forms the rigid wall part 16, the flexible wall part 7 being sealed to the rigid housing 6, 14 along a contour 23 of the rigid wall part 16, a portion of the rigid housing has a double function as a portion of the housing and as a boundary of the substance reservoir space 5.

The flexible wall part 7 has a shape such that, when the reservoir is in an unfilled condition while the pressure inside the reservoir space 5 is about equal to the pressure outside the reservoir space 5, the flexible wall 7 part extends closely along the rigid wall part 6 as indicated by a dashed line 7' in FIG. 2. That the flexible wall 7 part extends closely along the rigid wall part 6 when unpressured, provides the advantage, that the volume of the reservoir space 5 before filling is virtually zero, so that during filling no significant amount of air needs to be expelled from the reservoir space and the risk of air becoming trapped in the reservoir space 5 during filling is avoided. Moreover, the absence of significant volumes of air in the reservoir space 5 provides the advantage that when the pump 8 is activated, it is avoided that only air is pumped for a prolonged period of time.

Furthermore, the rigid wall part 6 has an at least partially concave surface facing the flexible wall part 7. Thus, when the reservoir is empty, the flexible wall part has a shape following a cavity bounded by the rigid wall part 16. Gradually inverting this shape allows the internal volume of the reservoir space 5 to accommodate to changes in the volume of substance therein but requires only relatively small deformations of the flexible wall part 7, so that the reservoir space accommodates easily to the amount of substance filled therein and dispensed therefrom and only little pressure is required to fill the reservoir.

The flexible wall part 7 is located between the main body 2 and an outer housing part 6 of the rigid housing 6, 14 to which outer part 6 it is connected along the contour 23 of the rigid wall part 16. Thus, the flexible wall part 7 is well shielded by the rigid housing part 6 to which it is connected when the cartridge 3 is mounted for use.

The outer housing part 6 of the rigid housing 6, 14 also forms an outer housing part of the appliance 1 when the cartridge 3 is connected to the main body 2 of the appliance 1. Thus, the cartridge is directly accessible from the outside and no separate cap covering the mounted cartridge 3 is required.

Since the flexible wall part 7 is located between the inner housing part 14 and the outer housing part 6 of the rigid housing 6, 14, to which it is connected along the contour 23 of the rigid wall part 16, it is also well shielded before the cartridge 3 is mounted to a main body 2. Thus, damage to the flexible wall part 7 and inadvertent pressing of substance out of the reservoir, for instance caused by a heavy object resting on top of the cartridge 3 while it is in a shopping bag is counteracted. Furthermore, the inner housing part 14 limits the extent to which the flexible wall part 7 can bulge out during filling and thereby accurately determines the amount of substance that can be filled into the reservoir and prevents the flexible wall part 7 from bulging out to such an extent, that the cartridge 3 cannot be mounted to the main body 2. Furthermore, the inner housing part forms a supplementary barrier layer covering the flexible wall part, so that permeation out of the cartridge 3 of constituents of the substance for which the flexible wall part 7 forms an insufficiently effective barrier is, at least to a large extent, prevented.

According to the present example, the rigid housing hermetically encapsulates the reservoir except for a passage to the pump 8. To achieve this, the rigid housing further includes a closure 21 closing off a passageway 15 in the inner housing part 14.

An effective seal between the inner housing part 14 and the outer housing part 6 is obtained in a particularly simple manner, because the flexible wall part 7 is sealed between the inner housing part 14 and the outer housing part 6 along the contour 23 of the rigid wall part 16. This can be achieved in a particularly efficient manner by connecting the inner and outer housing parts 6, 14 to each other (for instance by welding or by an adhesive) in such a manner, that the flexible wall part 7 is clamped between the inner and outer housing parts 6, 14 along the contour of the rigid wall part 16.

The rigid housing 6, 14 is provided with a passageway 15 for the passage of air to and out of a space 20 between the flexible wall part 7 and the rigid housing (in this example the inner housing part 14). Thus, air in the space 20 can escape when the reservoir is being filled.

After filling, the passageway 15 is sealed by means of the detachable and/or easily perforated closure 21, such as a sticker, to close off the passageway 15, thereby counteracting permeation of constituents of the substance. Preferably, the closure 21 hermetically closes off the space 20 between the flexible wall part 7 and the rigid housing, so that it needs to be removed or punctured, before use to allow significant amounts of substance to be drawn out of the reservoir without causing a vacuum therein. Preferably, the main body is equipped with a perforator (not shown) that perforates the closure 21 when the cartridge 3 is mounted to the main body 2. The closure 21 then also forms an indication that the cartridge 3 has been used.

A further indication whether the cartridge has been used is obtained by providing that at least the outer housing part 6 (and if the rigid wall part is distinct from the outer housing part, the rigid wall part as well) is at least partly transparent. Thus, it can be seen from the outside whether the reservoir is empty, because then the flexible wall part 7 extends closely along and/or is in contact with the rigid wall part 16. If the outwardly facing surface of the flexible wall part is of a tint and/or color contrasting strongly to the tint and/or colour of the substance in the reservoir, it can easily be seen whether the cartridge is empty or almost empty.

For making dismounting and mounting of cartridges 3 particularly simple to carry out, the cartridge 3 and the main body 2 are equipped with mutually co-operating magnetic coupling members 24 detachably holding the cartridge 3 and the main body 2 together. This feature may also be applied advantageously, if the reservoir space for holding the substance to be dispensed is not bounded by a flexible wall part and a rigid wall part, but is of particular advantage if the reservoir is an undetachable part of the cartridge.

The pumping chamber 22 is integrated in the cartridge 3 in a particularly efficient manner, since it is located between the inner housing part 14 and the outer housing part 6 of the rigid housing 6, 14 and a continuation of the flexible wall part 7 is sealed between the inner housing part 14 and the outer housing part 6 along a contour of the pumping chamber 22.

A seal of the pumping chamber 22 is obtained in a particularly efficient manner, since the pumping chamber 22 is located between an outer housing part 6 of the rigid housing 6, 14 and a continuation of the flexible wall part 7 and the continuation of the flexible wall part 7 forms the pumping membrane 17 bounding the pumping chamber 22.

The invention claimed is:

1. A cartridge detachably connectable to a main body of an appliance for personal care including for skin, dental or hair treatment, the cartridge comprising:
    a flexible wall part bounding a reservoir space for holding a substance to be dispensed comprising a liquid, a paste or a gel, the flexible wall part allowing a reservoir space volume to accommodate to a volume of the substance filled therein,
    a rigid wall part also bounding the reservoir space, and
    a rigid housing,
    wherein the flexible wall part is connected to the rigid housing along a contour of the rigid wall part, and
    wherein a portion of the rigid housing forms at least a portion of the rigid wall part, the flexible wall part being sealed to the rigid housing along the contour of the rigid wall part.

2. The cartridge claim 1, wherein at least an outer housing part of the rigid housing is at least partly transparent.

3. The cartridge of claim 1, wherein the flexible wall part has a shape such that, when the reservoir is in an unfilled condition, the flexible wall part extends closely along the rigid wall part.

4. The cartridge of claim 3, wherein the rigid wall part has an at least partially concave surface facing the flexible wall part.

5. The cartridge of claim 1, wherein the flexible wall part is located between the main body and an outer housing part of the rigid housing, and wherein the flexible wall part is connected to the outer housing part along the contour of the rigid wall part.

6. The cartridge of claim 1, wherein the flexible wall part is located between an inner housing part and an outer housing part of the rigid housing, and wherein the flexible wall part is connected to the outer housing part along the contour of the rigid wall part.

7. A cartridge detachably connectable to a main body of an appliance for personal care including for skin, dental or hair treatment, the cartridge comprising:
    a flexible wall part bounding a reservoir space for holding a substance to be dispensed comprising a liquid, a paste or a gel, the flexible wall part allowing a reservoir space volume to accommodate to a volume of the substance filled therein,
    a rigid wall part also bounding the reservoir space, and
    a rigid housing,
    wherein the flexible wall part is connected to the rigid housing along a contour of the rigid wall part,
    wherein the flexible wall part forms a seal between an inner housing part and an outer housing part of the rigid housing along the contour of the rigid wall part.

8. The cartridge of claim 7, wherein the rigid housing fully encapsulates the reservoir space.

9. The cartridge of claim 7, wherein the rigid housing is provided with a passageway for the passage of air to and out of a space within the cartridge between the flexible wall part and the rigid housing.

10. The cartridge of claim 9, wherein the rigid housing further comprises a closure sealing off the passageway, the closure being at least detachable or perforatable.

11. A cartridge detachably connectable to a main body of an appliance for personal care including for skin, dental or hair treatment, the cartridge comprising:
    a flexible wall part bounding a reservoir space for holding a substance to be dispensed comprising a liquid, a paste or a gel, the flexible wall part allowing a reservoir space volume to accommodate to a volume of the substance filled therein,
    a rigid wall part also bounding the reservoir space, and
    a rigid housing,
    wherein the flexible wall part is connected to the rigid housing along a contour of the rigid wall part,
    wherein the flexible wall part is clamped between the inner housing part and the outer housing part along the contour of the rigid wall part.

12. A cartridge detachably connectable to a main body of an appliance for personal care including for skin, dental or hair treatment, the cartridge comprising:
    a flexible wall part bounding a reservoir space for holding a substance to be dispensed comprising a liquid, a paste or a gel, the flexible wall part allowing a reservoir space volume to accommodate to a volume of the substance filled therein,
    a rigid wall part also bounding the reservoir space,
    a rigid housing, and
    a magnetic coupling member for detachably holding the cartridge to the main body of the appliance for personal care,
    wherein the flexible wall part is connected to the rigid housing along a contour of the rigid wall part.

13. An appliance for personal care for least one of skin, dental or hair treatment, comprising a main body, a dispensing structure for dispensing a substance comprising a liquid, a paste or a gel, and a cartridge, wherein the cartridge comprises:
    a flexible wall part bounding a reservoir space for holding a substance to be dispensed comprising a liquid, a paste or a gel, the flexible wall part allowing a reservoir space volume to accommodate to a volume of the substance filled therein,
    a rigid wall part also bounding the reservoir space,
    a rigid housing, and
    magnetic coupling members detachably holding the cartridge and the main body together,
    wherein the flexible wall part is connected to the rigid housing along a contour of the rigid wall part, the cartridge being detachably connected to the main body.

14. The appliance of claim 13, wherein at least an outer housing part of the rigid housing forms an outer housing part of the appliance when the cartridge is connected to the main body of the appliance.

15. The appliance of claim 13, wherein the cartridge comprises at least part of a pump for pumping the substance out of the reservoir space.

16. An appliance for personal care for least one of skin, dental or hair treatment, comprising a main body, a dispensing structure for dispensing a substance comprising a liquid, a paste or a gel, and a cartridge, wherein the cartridge comprises:
    a flexible wall part bounding a reservoir space for holding a substance to be dispensed comprising a liquid, a paste or a gel, the flexible wall part allowing a reservoir space volume to accommodate to a volume of the substance filled therein,
    a rigid wall part also bounding the reservoir space, and
    a rigid housing, wherein the flexible wall part is connected to the rigid housing along a contour of the rigid wall part, the cartridge being detachably connected to the main body, wherein the cartridge comprises at least part of a pump for pumping the substance out of the reservoir space, and wherein the pump comprises a pumping chamber located between an inner housing part and an outer housing part of the rigid housing and wherein a continuation of the flexible wall part is sealed between the inner housing part and the outer housing part along a contour of the pumping chamber.

17. An appliance for personal care for least one of skin, dental or hair treatment, comprising a main body, a dispensing structure for dispensing a substance comprising a liquid, a paste or a gel, and a cartridge, wherein the cartridge comprises:

a flexible wall part bounding a reservoir space for holding a substance to be dispensed comprising a liquid, a paste or a gel, the flexible wall part allowing a reservoir space volume to accommodate to a volume of the substance filled therein, a rigid wall part also bounding the reservoir space, and a rigid housing, wherein the flexible wall part is connected to the rigid housing along a contour of the rigid wall part, the cartridge being detachably connected to the main body, wherein the cartridge comprises at least part of a pump for pumping the substance out of the reservoir space, and wherein the pump comprises a pumping chamber located between an outer housing part of the rigid housing and a continuation of the flexible wall part and wherein the continuation of the flexible wall part forms a pumping membrane bounding the pumping chamber.

* * * * *